United States Patent
Bosworth

(10) Patent No.: US 11,482,330 B1
(45) Date of Patent: Oct. 25, 2022

(54) SYSTEM AND METHOD FOR POINT OF CARE BASED ON REAL-TIME PREDICTION OF ADDICTION TRIGGERS

(71) Applicant: Approved Assessments LLC, Plano, TX (US)

(72) Inventor: Annette Bosworth, Tea, SD (US)

(73) Assignee: Approved Assessments LLC, Plano, TX (US)

(*) Notice: Subject to any disclaimer, the term of this patent is extended or adjusted under 35 U.S.C. 154(b) by 530 days.

(21) Appl. No.: 16/101,174

(22) Filed: Aug. 10, 2018

Related U.S. Application Data

(60) Provisional application No. 62/540,940, filed on Aug. 3, 2017.

(51) Int. Cl.
G16H 50/20 (2018.01)
G06N 5/04 (2006.01)
G16H 10/20 (2018.01)
G06N 20/00 (2019.01)

(52) U.S. Cl.
CPC ............ *G16H 50/20* (2018.01); *G06N 5/047* (2013.01); *G06N 20/00* (2019.01); *G16H 10/20* (2018.01)

(58) Field of Classification Search
CPC ........ G16H 50/20; G16H 10/20; G06N 20/00; G06N 5/047
USPC .......................................................... 705/3
See application file for complete search history.

(56) References Cited

U.S. PATENT DOCUMENTS

| | | | |
|---|---|---|---|
| 2006/0036153 A1* | 2/2006 | Laken | A61B 5/164 600/410 |
| 2014/0100858 A1* | 4/2014 | Grollmuss | G16H 50/30 705/2 |
| 2016/0086500 A1* | 3/2016 | Kaleal, III | A61B 5/744 434/257 |
| 2016/0134429 A1* | 5/2016 | Shimada | G06Q 30/0282 715/753 |

(Continued)

OTHER PUBLICATIONS

Altman, et al., "The Altman Self-Rating Mania Scale." Biological Psychiatry 42.10 (Nov. 15, 1997): pp. 948-955.

(Continued)

*Primary Examiner* — Robert A Sorey
*Assistant Examiner* — Kimberly A. Sass
(74) *Attorney, Agent, or Firm* — Dorsey & Whitney LLP

(57) ABSTRACT

A system comprising an assessment engine configured to asynchronously transmit assessment questions to a user and, in response, receive a plurality of personal data from a user. A behavior module communicatively coupled to the assessment engine and operable to generate a behavior profile associated with the user based, at least in part, on the plurality of personal data. The behavior profile configured to identify one or more addiction habits of the user and respective one or more triggers operable to induce the user to desire the one or more addiction habits. A plurality of sensors positioned proximate the user to provide real-time measurements of one or more biological conditions of the user body. A prediction module communicatively coupled to the plurality of sensors, the prediction module operable to predict occurrence of the one or more triggers based on the behavioral profile and the real-time measurements of the one or more biological conditions of the user body.

17 Claims, 3 Drawing Sheets

(56) References Cited

U.S. PATENT DOCUMENTS

2016/0278682 A1* 9/2016 Khaligh-Razavi ..... G16H 50/20

OTHER PUBLICATIONS

Altman, et al., "Clinician-Administered Rating Scale for Mania." PsycTESTS Dataset (Jan. 1994): pp. 124-134.
Altman, et al., The Clinician-Administered Rating Scale for Mania (CARS-M): development, reliability, and validity. Biol Psychiatry. Jul. 1994; 36(2): pp. 124-134.
Anderson, et al., "Sleep Disturbance in Mental Health Problems and Neurodegenerative Disease." Nature and Science of Sleep NSS (May 2013): p. 61. Web.
Boudreaux, et al., "Impaired Personality Functioning and the Personality Inventory for DSM-5." PsycEXTRA Dataset (Jun. 2013).
Buschke, et al., "Screening for dementia with the Memory Impairment Screen." PsycTESTS Dataset (Jan. 15, 1999): pp. 231-238.
Calvo, et al., "Borderline Personality Disorder and Personality Inventory for DSM-5 (PID-5): Dimensional Personality Assessment with DSM-5." Comprehensive Psychiatry 70 (Jul. 2016): pp. 105-111.
Cella, et al., "The Patient-Reported Outcomes Measurement Information System (PROMIS) Developed and Tested Its First Wave of Adult Self-reported Health Outcome Item Banks: 2005-2008." Journal of Clinical Epidemiology 63.11 (Mar. 2010): 1179-194.
Clarke, et al., "DSM-5 Cross-cutting Symptom Measures: A Step towards the Future of Psychiatric Care?" World Psychiatry—13.3 (Oct. 2014): pp. 314-316.
Dakwar, et al., "The Utility of Attention-deficit/hyperactivity Disorder Screening Instruments in Individuals Seeking Treatment for Substance Use Disorders." 73.11 (Nov. 2012).
Denis, et al., "Inter-observer Reliability of DSM-5 Substance Use Disorders." Drug and Alcohol Dependence 153 (Aug. 2015): pp. 229-235.
Gierk, et al., "Assessing Somatic Symptom Burden: A Psychometric Comparison of the Patient Health Questionnaire—15 (PHQ-15) and the Somatic Symptom Scale—8 (SSS-8)." Journal of Psychosomatic Research 78.4 (Nov. 2015): pp. 352-355.
Jones, K. Dayle, "Dimensional and Cross-Cutting Assessment in the DSM-5." Journal of Counseling & Development 90.4 (Oct. 2012): pp. 481-487.
Kopak, et al., A Comparison of the DSM-5 and ICD-10 Cocaine Use Disorder Diagnostic Criteria. International Journal of Mental Health and Addiction Int J Ment Health Addiction 13.5 (Feb. 2015): pp. 597-602.
Labos, et al., "Comparing the Memory Impairment Screen (MIS) Test with the Memory Impairment Screen Deferred (MISD) for Detection of Amnestic Mild Cognitive Impairment (aMCI)." Alzheimer's & Dementia 9.4 (May 2013); section P2-244, pp. 445-446.
Martin, et al., "Truth or Consequences in the Diagnosis of Substance Use Disorders." Addiction 109.11 (Nov. 2014): pp. 1773-1778. Web.
Merchant, et al., "Variations in Substance Use Prevalence Est. & Need for Interventions Among Adult Emerg. Dept. Patients Based on Different Screening Strategies Using the ASSIST." West. Journal of Emerg. Med. WestJEM 17.3 (Mar. 2016): pp. 302-314.
Narrow, et al., "DSM-5 Field Trials in the United States and Canada, Part III: Development and Reliability Testing of a Cross-Cutting Symptom Assessment for DSM-5." American Journal of Psychiatry AJP 170.1 (Jan. 2013): pp. 71-82.
Nordin, et al., "Psychometric Evaluation and Normative Data for a Swedish Version of the Patient Health Questionnaire 15—Item Somatic Symptom Severity Scale." Scandinavian Journal of Psychology 54.2 (Jan. 2013): pp. 112-117.
Pilkonis, et al., "Item Banks for Measuring Emotional Distress From the Patient-Reported Outcomes Measurement Information System (PROMIS(R)): Depression, Anxiety, and Anger." Assessment 18.3 (Sep. 2011): pp. 263-283.
Proctor, et al., "Cocaine Use Disorder Prevalence: From Current DSM-IV to Proposed DSM-5 Diagnostic Criteria with Both a Two and Three Severity Level Classification System." Psychology of Addictive Behaviors 28.2 (Jun. 2014): pp. 563-567.
Saipanish, et al., "A Study of Diagnostic Accuracy of the Florida Obsessive-Compulsive Inventory—Thai Version (FOCI-T)." BMC Psychiatry 15.1 (Oct. 2015).
Shand, et al., "Predictors of Social Anxiety in an Opioid Dependent Sample and a Control Sample." Journal of Anxiety Disorders 24.1; (Jan. 2010): 49-54.
Spilsbury, et al., "Psychometric Properties of the Dimensions of Stressful Events Rating Scale." Traumatology 14.4 (Dec. 2008): pp. 116-130.
Stinchfield, et al., "Reliability, Validity, and Classification Accuracy of the DSM-5 Diagnostic Criteria for Gambling Disorder and Comparison to DSM-IV." J Gambl Stud Journal of Gambling Studies 32.3 (Sep. 2015): 905-22.
Storch, et al., "Florida Obsessive-Compulsive Inventory." PsycTESTS Dataset (Sep. 2007): pp. 851-859.
Unknown, By Practice Research and Policy Staff. "Substance Use Disordersand ICD-10-CM Coding." Http://www.apapracticecentral. org. American Psychiatric Association, (Oct. 9, 2015).
Unknown, https://www.keepingyouwell.com/Portals/32/docs/Patients%20and%20Visitors/sleepapneascreening.pdf.
Wenzel, Amy, Group Cognitive Therapy for Addictions. New York: Guilford, (Jul. 2012). pp. 50-79.
Wolff, et al., "Screening for Subst. Use Disorder Among Incar. Men w/Alcohol, Smoking, Subst. Involv. Screen. Test (ASSIST): A Comp. Anal. of Computer-Admin. & Interviewer-Admin. Modalities." Journal of Subst. Abuse Treatment 53 (Jun. 2015): p. 1-29.
Yang, et al., "A Screening Tool of Obstructive Sleep Apnea." Sleep Medicine Clinics 8.1 (Mar. 2013): pp. 65-72.

* cited by examiner

SYSTEM AND METHOD FOR POINT OF CARE BASED ON REAL-TIME PREDICTION OF ADDICTION TRIGGERS

CROSS-REFERENCE TO RELATED APPLICATION(S)

This application claims the benefit of U.S. Provisional Application No. 62/540,940 filed Aug. 3, 2017, which is incorporated herein by reference, in its entirety, for any purpose.

TECHNICAL FIELD

This disclosure generally relates to a system and method for accurately identifying individuals with addiction habits in addition to their specific triggers, and more specifically to predicting occurrence of triggers in real-time based, at least in part, on detected biological conditions of the user.

BACKGROUND OF THE DISCLOSURE

Currently, addiction assessments rely upon the thoughtful and truthful responses of an addict to identify those with a true problem. Once the problem of addiction is correctly identified, further assessment questions generate a recommended treatment plan. Current methods rely on the integrity and recollection of the addict for the assessor to determine whether an addiction patterns exists and the events that may trigger such addiction.

In particular, a current process to identify addicts relies on in-person interviews to gauge the truthfulness of the client. The industry's flawed assumption that a provider can determine truthfulness through the body language, responses to questions and a mythical skill to get clients to tell the truth has led to a massive gap in identifying those with a true problem. Because addicts master their skill of hiding their addiction from others, there is a need for an automated pattern recognition system to accurately identify those with addiction based on their behavior collected by the system during the interview.

Additionally, there is a further need for real-time prediction and monitoring of triggering events before they occur. Predicting triggering events and implementing a timely intervention is needed to reduce recidivism rates among addicts. Currently, it is not possible for a therapist or physician to physically monitor the addict 24/7. Because addicts cannot see behavioral patterns in themselves and instead rely on a $3^{rd}$ party for such analysis, there is a need for an automated pattern recognition system to accurately predict behavior patterns even when a $3^{rd}$ party is not physical present with the addict.

SUMMARY OF THE INVENTION

According to one aspect, a non-transitory computer readable medium having a memory and instructions stored therein that when executed by a processor performs a method comprising collecting a plurality of personal data from a user in response to assessment questions; generating a behavior profile associated with the user based, at least in part, on the plurality of personal data collected from the user, the behavior profile configured to identify one or more addiction habits of the user and respective one or more triggers operable to induce the user to desire the one or more addiction habits; and predicting occurrence of the one or more triggers in response to real-time bio-sensor feedback of the user.

According to another aspect, a system comprising an assessment engine configured to asynchronously transmit assessment questions to a user and, in response, receive a plurality of personal data from a user; a behavior module communicatively coupled to the assessment engine, the behavior module operable to generate a behavior profile associated with the user based, at least in part, on the plurality of personal data; the behavior profile configured to identify one or more addiction habits of the user and respective one or more triggers operable to induce the user to desire the one or more addiction habits; a plurality of sensors positioned proximate the user to provide real-time measurements of one or more biological conditions of the user body; and a prediction module communicatively coupled to the plurality of sensors, the prediction module operable to predict occurrence of the one or more triggers based on the behavioral profile and the real-time measurements of the one or more biological conditions of the user body.

BRIEF DESCRIPTION OF THE DRAWINGS

Reference will now be made to the attached drawings, when read in combination with the following specification, wherein like reference numerals refer to like parts throughout the several views, and in which.

DETAILED DESCRIPTION

Figure 1:
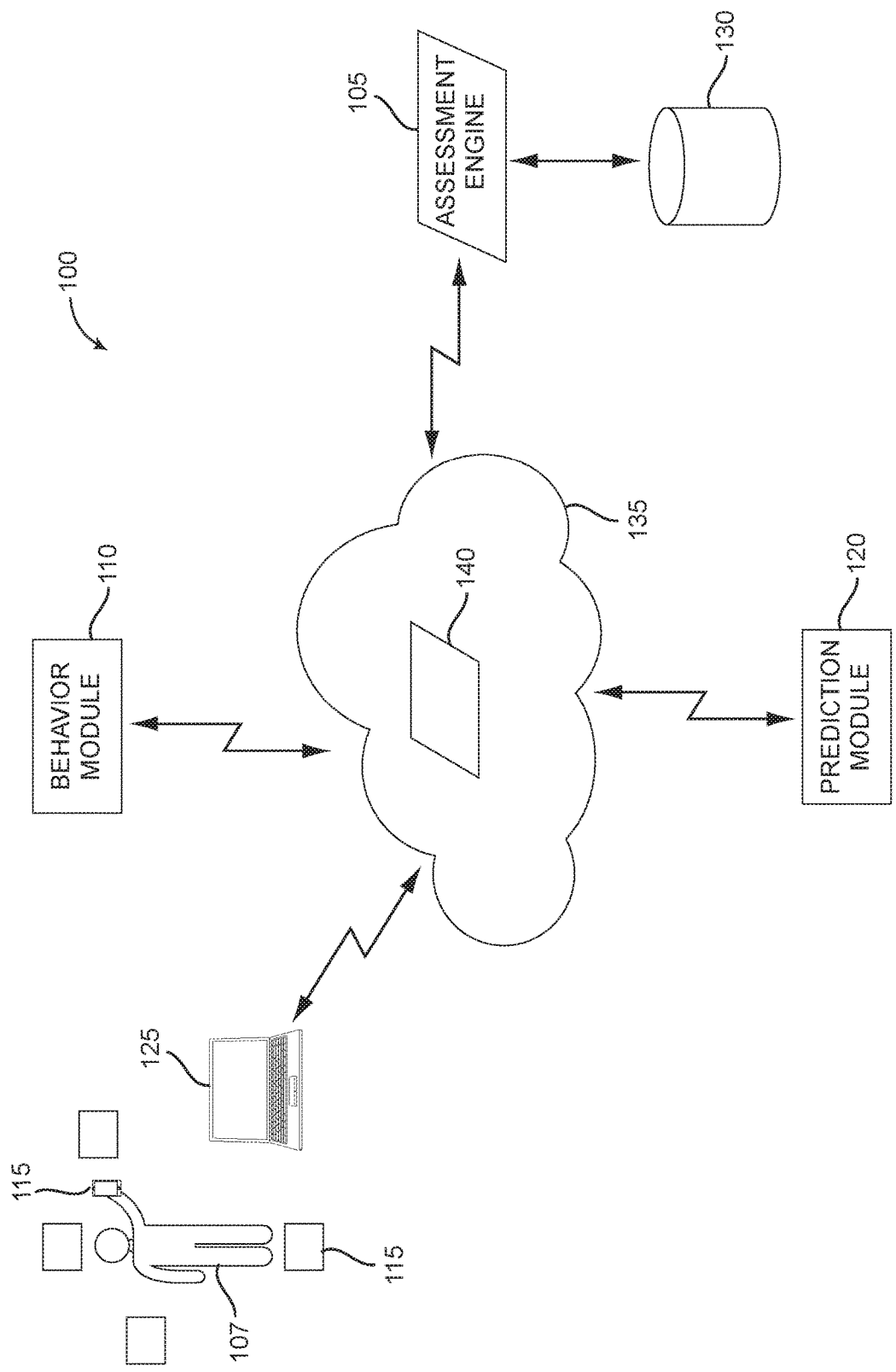
FIG. 1 is a schematic illustration of a behavior profiling system to analyze users having an addiction, according to one illustrated embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Various examples of embodiments of the invention will now be described. The following description provides specific details for a thorough understanding and enabling description of these examples. One skilled in the relevant art will understand, however, that embodiments of the invention may be practiced without many of these details. Likewise, one skilled in the relevant art will also understand that embodiments incorporate many other obvious features not described in detail herein. Additionally, some well-known structures or functions may not be shown or described in detail below, so as to avoid unnecessarily obscuring the relevant description.

The terminology used herein is to be interpreted in its broadest reasonable manner, even though it is being used in conjunction with a detailed description of certain specific examples of the invention. Indeed, certain terms may even be emphasized below; any terminology intended to be interpreted in any restricted manner will, however, be overtly and specifically defined as such in this Detailed Description section.

The figures along with the following discussion provide a brief, general description of a suitable environment in which embodiments of the invention can be implemented. Although not required, aspects of various embodiments are described below in the general context of computer-executable instructions, such as routines executed by a general purpose data processing module, e.g., a networked server computer, cloud server, mobile device, tablet, or personal computer. Those skilled in the relevant art will appreciate that embodiments can be practiced with other communications, data processing, or computer system configurations, including: Internet appliances, hand-held devices (including smart phones and tablets), wearable computers, all manner of corded, landline, fixed line, cordless, cellular or mobile phones, smart phones, multi-processor systems, microprocessor-based or programmable consumer electronics, set-top boxes, network PCs, mini-computers, mainframe computers, media players and the like. Indeed, the terms "computer," "server," and the like are generally used interchangeably herein, and refer to any of the above devices and systems, as well as any data processor.

While embodiments of the invention, such as certain functions, may be described as being performed on a single device, embodiments of the invention can also be practiced in distributed environments where functions or modules are shared among disparate processing devices, which are linked through a communications network, such as, for example, a Local Area. Network (LAN), Wide Area. Network (WAN), the Internet, Bluetooth, and Zigbee. In a distributed computing environment, program modules may be located in bath local and remote memory storage devices.

Embodiments of the invention may be stored or distributed on tangible computer-readable media, including magnetically or optically readable computer discs, cloud servers, hard-wired or preprogrammed chips (e.g., EEPROM semiconductor chips), nanotechnology memory, biological memory, or other data storage media. Alternatively or additionally, computer implemented instructions, data structures, screen displays, and other data under aspects of embodiments of the invention may be distributed over the Internet and via cloud computing networks or on any analog or digital network (packet switched, circuit switched, or other scheme).

The computer readable medium stores computer data, which data may include computer program code that is executable by a computer, in machine readable form. By way of example, a computer readable medium may comprise computer readable storage media, for tangible or fixed storage of data, or communication media for transient interpretation of code-containing signals. Computer readable storage media, as used herein, refers to physical or tangible storage (as opposed to signals) and includes without limitation volatile and non-volatile, removable and non-removable media implemented in any method or technology for the tangible storage of information such as computer-readable instructions, data structures, program modules or other data. Computer readable storage media includes, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

Embodiments of the invention are described herein with reference to operational illustration of modules and flowcharts having functional blocks to illustrate methods employed by modules to identify addiction habits of a user and continuously monitor for triggers that may instigate the addictive behavior, Additionally, the modules and flowcharts illustrate methods for timely intervention upon detection of at least one of the triggers, thereby preventing recidivism. It will be understood that each of the modules, blocks, and combinations thereof may be implemented by analog or digital hardware and computer program instructions. The computer program instructions may be provided to a processor of a general purpose computer, special purpose computer, application-specific integrated circuit (ASIC), or other programmable data processing apparatus such that the instructions, which execute via the processor of the computer or other programmable data processing apparatus, implements the functions/acts specified in the functional blocks of the flowcharts and/or the operational modules.

In some embodiments, the methods illustrated by the functional blocks may occur out of the order noted in the operational illustration of the modules. For example, two blocks shown in succession may be executed substantially concurrently. Alternatively and/or additionally, the blocks may be executed in reverse order, blocks may be removed, and/or blocks may be added.

A module is a software, hardware, or firmware (or combination thereof) system, process or functionality, or component thereof, that performs or facilitates the processes, features, and/or functions described herein. A module may include sub-modules. Software components of a module may be stored on a computer readable medium. Modules may be integral to one or more servers, or be loaded and executed by one or more servers. One or more modules may be grouped into an application.

FIG. 1 shows a schematic illustration of a dynamic behavior profiling system 100 to analyze users having an addiction, according to one embodiment.

The behavior profiling system 100 comprises an assessment engine 105 communicatively coupled to a user 107, a behavior module 110 communicatively coupled to the assessment engine 105, a plurality of sensors 115 coupled proximate the user 107, and a prediction module 120 communicatively coupled to the plurality of sensors 115, It will be appreciated by those of ordinary skill in the art that various components within the behavior profiling system 100 may be communicatively coupled to one another either via direct wired or wireless transmission or transmission through a network 135. The network 135 may, for example, take a form of a wired or wireless LAN, WLAN, Internet, or Internet of Things (IoT) network (e.g., ZIGBEE, BLUETOOTH).

The assessment engine 105 may be configured to transmit a plurality of assessment questions to the user 107 via an interface 125. The questions are, for example, aimed at identifying whether the user has addictive behavior or mental health issues. The plurality of questions may be stored in an assessment database 130 communicatively coupled to the assessment engine 105. The assessment database 130 may be embedded within the assessment engine 105 or positioned remote from the assessment engine 105. The assessment database 130 includes the plurality of assessment questions mentioned above. The plurality of assessment questions may comprise subsets of questions specifically tailored to stimulate discrete portions of the user's 107 (i.e., addict or mental health sufferer) brain. Based on the user's 107 cumulative responses to each of the subsets of questions, respective portions of the user's brain may be evaluated and assessed.

It is advantageous to segment and analyze various portions of the brain in the interest of formulating an effective treatment plan, should the user 107 be diagnosed with addictive behavior or a mental health issue. It will be noted that any reference to "addictive behavior" or "addiction" throughout this disclosure encompasses any type of addictive behavior such as, for example, alcohol, drug, tobacco, or caffeine addiction to name a few. The assessment may encompass a mental health screening which includes: DEPRESSION, ANGER, MANIA, ANXIETY, SOMATIC SYMPTOMS, SUICIDAL IDEATIONS, PSYCHOSIS, SLEEP, SLEEP APNEA, LITERACY SCREEN, MEMORY, REPETITIVE THOUGHTS AND BEHAVIORS, DISSOCIATION, and PERSONALITY FUNCTION.

Additionally and/or alternatively, the assessment may encompass addiction in the form of substance abuse, such as, for example: ALCOHOL, OPIATES, CANNABIS, SEDATIVES, COCAINE, STIMULANTS, HALLUCINOGENS, NICOTINE, INHALANTS, DESIGNER DRUGS, GAMBLING, AND FOOD (E.G., HIGH CARBOHYDRATE, HIGH FAT, HIGH SUGAR, ETC.).

The assessment questions may seek to extract personal data from the user. The personal data may, for example, include Demographics, Past Medical History, Past Mental Health History, Past Surgical History, Current Medical Concerns, Traumatic Brain Injury History, Family History, Sexual History, Educational/Vocational History, Financial History, Military History/Status, Spirituality/Relationships, Sobriety/Relapse/Treatments, and Legal History to name a few.

The assessment engine 105 may asynchronously transmit the questions to the user via the interface 125. As will be discussed in more detail below, asynchronous transmission of the questions may allow for the assessment engine 105 to vary subsequent questions based on past responses. The interface 125 may take the form of a graphical user interface (GUI) on a computing device, for example. The GUI may be embedded within any form of computing device known in the art. In some embodiments, the GUI may embed various graphical representations embedded within the questions and/or choices for the user 107 to select, making it easier and/or efficient for the user 107 to formulate an accurate response that best characterizes the circumstance. In other words, a question might seek to determine the user's 107 feelings, emotions, or thoughts in response to a graphical representation of a specific circumstance. For example, one of the assessment questions may include a graphical rendering of a woman resting on the steps. The graphical rendering may be intentionally vague prompting the examiner's brain to fill in the missing parts of the sketch. The user 107 is asked to select a choice that best represents the woman's emotional state in the graphical rendering (e.g., Sad face, Happy face, Angry face, etc.

The behavior module 110 is operable to create a behavior profile associated with the user 107. The behavioral profile may be based, at least in part, on the user's 107 substantive responses to the assessment questions. The behavior profile is configured to identify one or more addiction habits or mental health issues associated with the user 107 along with respective one or more triggers. The one or more triggers may be events or stress components in the user's life where exposure increases the likelihood of initiating an addictive behavior. For example, the one or more triggers may comprise having to work overtime more than three times a week, observing a friend indulging in an alcoholic beverage, being in close proximity to a bar or casino, observing parents being abusive to one another, etc.

The plurality of sensors 115 may be any type of sensor, for example, bio-sensors, which detect various types of bio-measurements associated with the physical condition of the user 107. The various types of bio-measurements may include: body temperature, heart rate, breathing rate, blood pressure, perspiration levels, to name a few. The plurality of sensors 115 may include point-of-care devices that analyze various bio-markers such as, for example, blood, saliva, serum, or the like. The plurality of sensors 115 may, for example, be located proximate the user 107. In one embodiment, the plurality of sensors 115 may be within close proximity to the user 107 or physically coupled to the user 107 to sense physical conditions associated with the user's body in real-time. The sensors 115 may further include transceiver circuitry operable to transmit measurements to a remote processor. In other embodiments, at least some of the plurality of sensors 115 may be re-programmable. In other words, the re-programmable sensors 115 may be configured by a user to detect a first set of physical conditions associated with the user 107, and then later re-configured to detect a second set of physical conditions associated with the user 107, The first and second set of physical conditions may be different. Additionally, at least one of the sensors 115 may be a mobile device, such as a smart phone or wearable device with geolocation determination capability.

The prediction module 120 may be communicatively coupled to the plurality of sensors 115. As indicated above, the prediction module 120 may be communicatively coupled to the plurality of sensors via the network 135. The prediction module 120 may be operable to predict occurrence of the one or more triggers based on the behavioral profile generated by the behavior module 110 and the real-time one or more of the bio-measurements associated with the physical condition of the user 107. In one embodiment, the user's 107 ombudsman, such as, for example, physician, mental health care provider, or social worker, receives real-time communication from the prediction module 120. It will be noted the term "ombudsman" refers to a lead advocate for the user (e.g., addict) 107 and includes a physician, social worker, religious leader, and mental health care provider to name a few. In one example, the ombudsman may refer to a past-addict who has recovered from an addiction or even a general member of the public who is a "do-gooder." The prediction module 120 may be communicatively coupled to a mobile device (e.g., smart phone, tablet, laptop, notebook) associated with the user's 107 ombudsman. For example, the user's 107 ombudsman may receive real-time indication of a predicted occurrence of the one or more triggers via the mobile device. In response to the real-time prediction, the user's 107 ombudsman may immediately intervene to prevent the user 107 from engaging in at least one of his/her addictive behaviors. Consequently, the behavior profiling system 100 allows for timely intervention to prevent recidivism of the user 107. In one example, the prediction module 120 may receive geolocation information from at least one of the sensors 115 and determine the user's real-time location to be proximate a pub. If the behavioral profile of that user 107 indicates close proximity to a pub as one of the triggers, then the prediction module 120 may alert the social worker who, in turn, intervenes. By way of example, real-time intervention by the social worker may take the form of a phone call to the user 107 and/or an actual visit with the user 107. In one embodiment, the prediction module 120 may leverage an application on a mobile device to alert the user 107 and/or ombudsman of a detected trigger. The real-time detection of the trigger event coupled with the behavior profile allows the social worker or physician to strategically intervene to prevent the user from engaging or re-engaging in behavior that leads to addiction.

Additionally, the dynamic behavior profiling system 100 may further include a machine learning module 140 communicatively coupled to at least one of the assessment engine 105 and the behavior module 110. The machine learning module 140 may be embedded within the network 135 or located locally on any of the dynamic behavior profiling system 100 components. The machine learning module 140 is operable to continuously monitor and detect behavior patterns of the user 107, such as social media patterns. In one embodiment, the machine learning module 140 applies a machine learning algorithm to social media accounts the user 107 is associated with. The social media accounts may, for example, include FACEBOOK, TWITTER, SNAPCHAT, WHATSAPP, etc. Additionally, the machine learning module 140 may also have access to text messages on the user's 107 mobile device.

As will be appreciated by those of ordinary skill in the art, humans have difficulty finding or noticing patterns in themselves. As such, the machine learning module 140, by way of scraping social networking sites of the user 107 and/or the user's 107 mobile device, may detect patterns of behavior advantageous in generating a more accurate behavior profile. For example, the user 107 may not be aware that he/she engages in addictive behavior in response to specific triggers. However, analysis of events surrounding the addictive behaviors may show a particular behavior pattern. If the user 107, for example, consistently posts on social media sites photos of herself at a rock concert proximate to her messaging with friends about the need for alcohol and/or proximate to her posting photos of herself at a bar, the machine learning module 140 may pick up on that behavior pattern. The pattern recognitions determined by the machine learning module 140 may be employed by the behavior module 110 to generate the behavior profile and more accurately reflect the one or more triggers associated with the addictive behavior. Alternatively and/or additionally, the behavior patterns recognized by the machine learning module 140 may reveal additional addictive behaviors not readily recognizable in response to the assessment questions.

As mentioned above, the machine learning module 140 may additionally be communicatively coupled to the assessment engine 105. While generating the assessment questions, the assessment engine 105 may leverage the behavior patterns resulting from the machine learning module 140 analysis of social media sites. In other words, the assessment engine 105 may determine subsequent ones of the plurality of assessment questions to transmit to the user 107 based on the detected social media patterns of the user 107 by the machine learning module 140. Additionally, the assessment engine 105 may calculate the user 107 response times to each of the assessment questions. Based on the calculated response times, the assessment engine 105 may determine subsequent ones of the plurality of assessment questions to transmit to the user 107. For example, if the user 107 takes a notably, longer amount of time to respond to one or more questions from a first subset of questions directed towards a specific portion of the user's brain, this may be indicative of a level of truthfulness or accuracy associated with the user's 107 response.

For example, the assessment engine 105 may associate a low truthfulness or low accuracy score with a longer-timed response than with a shorter-timed response. Of course, it will be understood by those of ordinary skill in the art, the amount of time required to respond to questions varies on complexity and the individual him/herself. However, the machine learning module 140 may operate to learn a pattern of the user's 107 response time for each set of assessment questions. In response to the user's response times substantially veering away from the user's average response time pattern, the assessment engine 105 may incorporate that data point when generating follow-up questions.

Additionally, the behavior module 110 may integrate the truthfulness or accuracy, level associated with respective ones of the assessment responses when generating the behavior profile. As discussed above, the behavior module 110 may generate the behavior profile for the user 107 based on responses to the assessment questions and the behavior pattern recognitions from social media sites as identified by the machine learning module 140. In one embodiment, the behavior module 110 may allocate a greater weight to responses having a high truthfulness level over responses having a lower truthfulness level.

Figure 2:
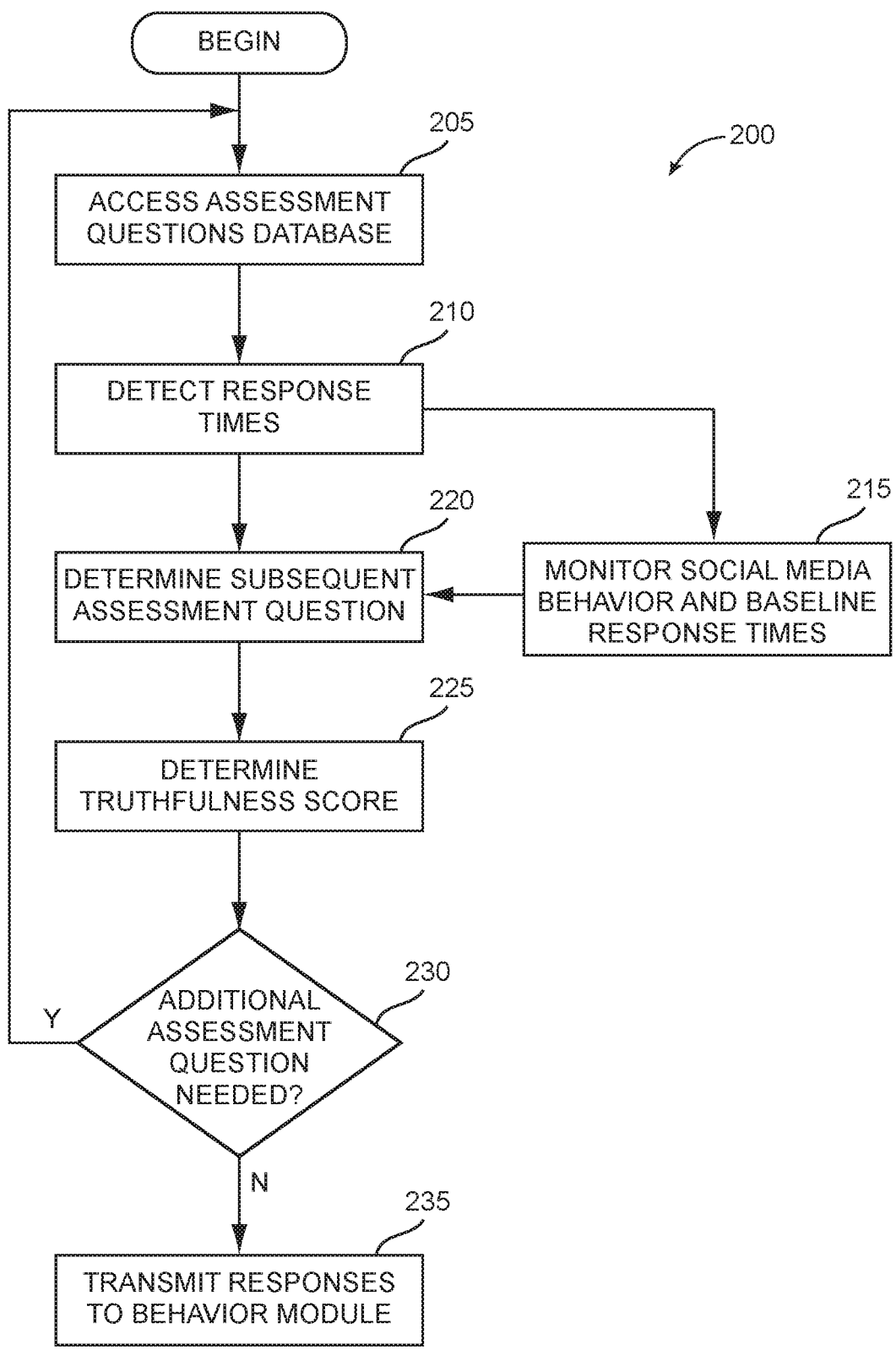
FIG. 2 is a flowchart of a method for creating a behavior profile associated with the user, according to one illustrated embodimen.

FIG. 2 shows a flowchart of a method 200 for creating the behavior profile associated with the user 107, according to one illustrated embodiment. The method 200 begins in response to the user 107 engaging with the behavior profiling system 100. In one embodiment, engaging with the behavior profiling system 100 may include the user 107 logging in to a web-based application via the interface (e.g. GUI) of a computing device. In one example, the web-based application may comprise a mobile application on the user's 107 mobile device.

At 205, the assessment engine 105 may access the assessment database 130 to begin asynchronous transmission of assessment questions to the user 107 via the interface 125. As mentioned above, the assessment questions comprise subsets of questions tailored to stimulate discrete portions of the user's 107 brain.

At 210, the assessment engine 105 calculates the user 107 response times to respective ones of the plurality of assessment questions. The assessment engine 105 may transmit the detected response times to the machine learning module 140. At 215, the machine learning module 140 may operate to learn a pattern of the user's 107 response times for each subset of assessment questions. For example, based on past responses of the user 107 or previous users for a specific subset of assessment questions, the machine learning module 140 may extract a baseline response time. Additionally, the machine learning module 140 continuously monitors social media accounts associated with the user 107 to further identify behavior patterns.

At 220, the assessment engine 105 may receive the baseline response times for respective ones of the assessment questions and the social media behavior patterns of the user 107 from the machine learning module 140. In response to the user's response substantially veering away from the baseline response times coupled with the social media behavior patterns of the user 107, the assessment engine 105 may determine an appropriate subsequent assessment question to asynchronously transmit to the user 107.

At 225, the assessment engine 105 may associate a truthfulness or accuracy score with each of the responses to the assessment questions. If the detected response time is substantially greater than the baseline response time, as determined by the machine learning module 140, the assessment engine 105 may associate a low truthfulness or low accuracy score with that response. On the other hand, if the detected response time is substantially less than or equivalent to the baseline response time, the assessment engine 105 may associate a high truthfulness score or high accuracy score with that response.

At 230, the assessment engine 105 asynchronously transmits the subsequent assessment question to the user 107 via the GUI, if additional assessment questions are needed to evaluate the user's 107 brain functionality. Otherwise, the method 200 passes control to 235.

At 235, the assessment engine 105 transmits the user's assessment question responses to the behavior module 115, The behavior module 115 may create the behavior profile associated with the user 107 based on the responses to the assessment questions. The behavior module 115 may additionally incorporate the behavior pattern recognitions from social media sites, as identified by the machine learning module 140, into the creation of the behavior profile. In particular, the behavior module 110 may integrate the truthfulness or accuracy level associated with respective ones of the assessment responses when generating the behavior profile. In one embodiment, the behavior module 110 may allocate a greater weight to responses having a high truthfulness level over responses having a lower truthfulness level.

Figure 3:
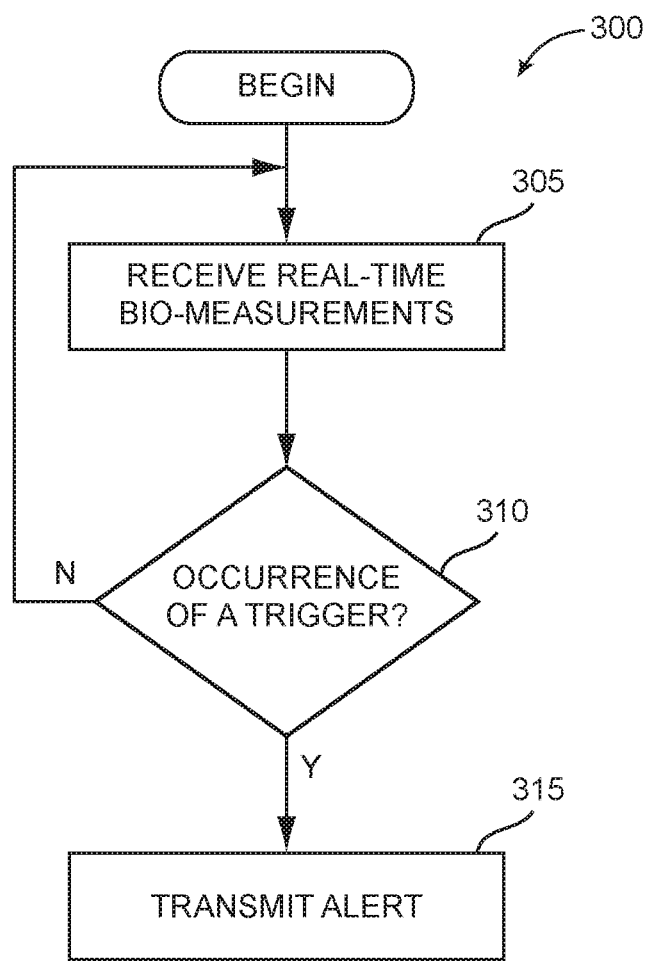
FIG. 3 is a flowchart of a method for alerting the user and/or social worker in response to predicting occurrence of at least one of the triggers, according to one illustrated embodiment.

FIG. 3 shows a flowchart of a method 300 for alerting the user 107 and/or social worker in response to predicting occurrence of at least one of the triggers, according to one illustrated embodiment. The method 300 may, for example, begin in response to the prediction module 120 receiving the behavior profile from the behavior module 110. The behavior profile may be continuously received while being updated by the behavior module 110 in response to updates in the learned behavioral patterns of the user 107. As discussed above, the behavior profile is configured to identify one or more addiction habits or mental health issues associated with the user 107 along with respective triggers. The triggers may be events or stress components in the user's life where exposure to at least one of the triggers increases the likelihood of initiating an addictive behavior. One exemplary trigger may be low hours of sleep within a 24-hour period. Additionally, the behavior profile may be continuously transmitted to the user 107 and/or the ombudsman, along with specific steps to help the user 107 refrain from relapsing into an addictive behavior pattern.

At 305, the prediction module 120 receives, in real-time, the bio-measurements associated with the physical condition of the user 107. As mentioned above, the bio-measurements may be body temperature, heart rate, breathing rate, blood pressure, perspiration levels, blood glucose level, blood ketones, and/or urine ketones to name a few, Additionally, at least one of the plurality of sensors 115 may provide geolocation information associated with the user 107 in real-time.

At 310, based on the real-time bio-measurements and the continuously updated behavior profile, the prediction module 120 predicts whether at least one of the triggers has occurred or is anticipated to occur in the near future. If the prediction module 120 predicts occurrence of one of the triggers, control passes to 315. Otherwise, control passes back to 305.

At 315, the prediction module 120 transmits an alert to the user's 107 ombudsman. The alert may be a communication transmitted to the mobile device associated with the user's 107 ombudsman. Alternatively and/or additionally, the communication alert may be transmitted to a mobile device associated with the user 107. The communication may take the form of at least one of a text message, voice call, alarm, or the like. In response to the real-time prediction, the user's 107 ombudsman may timely intervene to prevent the user 107 from engaging in at least one of his/her addictive behaviors in light of the detected trigger. For example, if the user 107 has a gambling addiction, his/her trigger may be physically being within 1000 ft or so of a casino. When at least one of the sensors 115 detects the user's geolocation within that trigger range, the user 107 and/or social worker may receive the communication alert. Alternatively, detecting a bio-measurement of a high heart rate may, for example, indicate the user 107 is currently experiencing one of the trigger events. Whether the prediction module 120 detects a current trigger event or a near-term trigger event, the prediction module 120 may implement the intervention policy by, for example, alerting the social worker to intervene.

Having described some embodiments of the invention, additional embodiments will become apparent to those skilled in the art to which it pertains. Specifically, although reference was made throughout the specification and drawings to a user having an addiction, it will be appreciated that the system 100 and method embodiments are also relevant to any other type of users that require monitoring for potential behavioral triggers and require timely intervention. The embodiment of the addict was described merely to readily convey various aspects of the behavior profiling system 100 and method as it pertains to point-of-care based on real-time prediction of addiction triggers, but was not intended to limit the system 100 in any way. For example, the behavior profiling system 100 may be advantageous to folks required to consume prescription medication on a daily basis. In this example, the user's physical condition may be monitored via the sensors to determine a change in various physical or biological characteristics in response to failure to consume prescribed medicine in a timely manner. In another example, the behavior profiling system 100 may be advantageous to users having anger management issues, where continuous monitoring of bio-measurements related to the physical condition of the user may predict an imminent anger outbreak. In yet another example, the behavior profiling system 100 may notice that upon a defined number of consecutive nights of decreased sleep, the user 107 displays excessive use of anger.

While the particular methods, devices and systems described herein and described in detail are fully capable of attaining the above-described objects and advantages of the invention, it is to be understood that these are example embodiments of the invention and are thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular means "one or more" and not "one and only one", unless otherwise so recited in the claim.

It will be appreciated that modifications and variations of the invention are covered by the above teachings and within the purview of the appended claims without departing from the spirit and intended scope of the invention.

What is claimed is:

1. A non-transitory computer readable medium having a memory and instructions stored therein that when executed by a processor performs a method comprising:
    asynchronously transmitting a plurality of assessment questions to a user for identifying whether the user has addictive behavior, wherein said asynchronously transmitting comprises: presenting, via a graphical user interface, a first subset of assessment questions designed to stimulate a first portion of a user's brain; comparing response times of the user's responses to the first subset of assessment questions to baseline response times; based, at least in part, on said comparing, selecting a second subset of assessment questions designed to stimulate a second portion of the user's brain; and presenting the second subset of assessment questions on the graphical user interface;

based, at least in part, on the user's responses to the first subset and second subset of assessment questions, generating a behavior profile of the user that identifies one or more addiction habits of the user and respective one or more addiction triggers operable to induce the user to desire the one or more addiction habits;

receiving real-time bio-sensor feedback from the user;

predicting occurrence of the one or more addiction triggers in response to real-time bio-sensor feedback of the user; and initiating a real-time communication upon prediction of the occurrence of the one or more addiction triggers.

2. The non-transitory computer readable medium of claim 1, wherein said selecting the second subset of assessment questions is further based on detecting social media patterns of the user.

3. The non-transitory computer readable medium of claim 2, wherein said generating the behavior profile includes identifying patterns of behavior from social media patterns of the user.

4. The non-transitory computer readable medium of claim 1, wherein said generating the behavior profile further includes applying a greater weight to responses associated with longer response times than to responses associated with shorter response times.

5. The non-transitory computer readable medium of claim 1, wherein the real-time bio-sensor feedback includes at least one of heart rate, breathing rate, or body temperature.

6. The non-transitory computer readable medium of claim 1, further comprising receiving geolocation information from the user in real-time, and wherein the predicting of the occurrence is based further on the received geolocation information of the user.

7. The non-transitory computer readable medium of claim 1, wherein the behavior profile is based further on personal data of the user including at least one of medical, behavioral, or familial history.

8. The non-transitory computer readable medium of claim 1, wherein the real-time communication comprises transmission to someone other than the user.

9. A system comprising:

a graphical user interface;

one or more processors configured to asynchronously present, on the graphical user interface, a first subset of assessment questions designed to stimulate a first portion of a user's brain and based, at least in part, on a comparison of response times of the user's responses to the first subset of assessment questions to baseline response times, select and present a second subset of assessment questions designed to stimulate a second portion of the user's brain, wherein the one or more processors are further configured;

to generate a behavior profile associated with the user based, at least in part, on the user's responses to the first subset and second subset of assessment questions, the behavior profile configured to identify one or more addiction habits of the user and respective one or more addiction triggers operable to induce the user to desire the one or more addiction habits; and a plurality of sensors positioned proximate the user to provide real-time measurements of one or more biological conditions of the user body;

wherein the one or more processors are communicatively coupled to the plurality of sensors and operable to predict occurrence of the one or more addiction triggers based on the behavioral profile and the real-time measurements of the one or more biological conditions of the user's body.

10. The system of claim 9, further comprising a machine learning module communicatively coupled to the one or more processors and configured to detect social media patterns of the user.

11. The system of claim 10, wherein the one or more processors are configured to determines the second subset of the assessment questions based further in part on the detected social media patterns of the user.

12. The system of claim 9, wherein the one or more processors are configured to apply a greater weight to responses associated with longer response times than to responses associated with shorter response times.

13. The system of claim 10, wherein the one or more processors are communicatively coupled to the machine learning module and configured to generate the behavior profile based, at least in part, on the social media patterns of the user.

14. The system of claim 9, wherein the real-time measurements of the one or more biological conditions of the user body comprise at least one of heart rate, breathing rate, perspiration level, or body temperature.

15. The system of claim 9, wherein at least one of the plurality of sensors further detects geolocation of the user in real-time.

16. The system of claim 9, wherein the one or more processors are configured to generate the behavior profile base further in part on personal data of the user comprising at least one of medical, behavioral, or familial history of the user.

17. The system of claim 9, wherein the one or more processors are operable to alert at least one of the user, mental health physician, or a social worker in response to prediction of the occurrence of the one or more addiction triggers.

* * * * *